US012635972B2

(12) United States Patent
Mihajlovic et al.

(10) Patent No.: US 12,635,972 B2
(45) Date of Patent: May 26, 2026

(54) SYSTEMS AND METHODS FOR TRACKING A TOOL IN AN ULTRASOUND IMAGE

(71) Applicant: KONINKLIJKE PHILIPS N.V., Eindhoven (NL)

(72) Inventors: Nenad Mihajlovic, Eindhoven (NL); Arash Pourtaherian, Eindhoven (NL); Michel Paul Barbara van Bruggen, Helmond (NL); Gary Cheng-How Ng, Redmond, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 700 days.

(21) Appl. No.: 17/276,349

(22) PCT Filed: Sep. 11, 2019

(86) PCT No.: PCT/EP2019/074149
§ 371 (c)(1),
(2) Date: Mar. 15, 2021

(87) PCT Pub. No.: WO2020/053237
PCT Pub. Date: Mar. 19, 2020

(65) Prior Publication Data
US 2022/0039773 A1      Feb. 10, 2022

Related U.S. Application Data

(60) Provisional application No. 62/731,122, filed on Sep. 14, 2018.

(30) Foreign Application Priority Data

Oct. 15, 2018      (EP) ..................................... 18200503

(51) Int. Cl.
*A61B 8/08* (2006.01)
*A61B 8/00* (2006.01)
*A61B 90/00* (2016.01)

(52) U.S. Cl.
CPC ............ *A61B 8/0841* (2013.01); *A61B 8/466* (2013.01); *A61B 8/483* (2013.01); *A61B 90/36* (2016.02);
(Continued)

(58) Field of Classification Search
CPC ....... A61B 8/0841; A61B 8/466; A61B 8/483; A61B 90/36; A61B 2090/367;
(Continued)

(56) References Cited

U.S. PATENT DOCUMENTS 5,582,173 A      12/1996   Li
5,997,479 A      12/1999   Savord et al.
(Continued)

FOREIGN PATENT DOCUMENTS

WO      2018050885 A1      3/2018

OTHER PUBLICATIONS

Waine, et al., "3D Shape Visualization of Curved Needles in Tissue from 2D Ultrasound Images using RANSAC", 2015 IEEE International Conference on Robotics and Automation, Washington State Convention Center, Seattle, Washington, May 26-30, 2015, pp. 4723-4728.
(Continued)

*Primary Examiner* — Keith M Raymond
*Assistant Examiner* — Amy Shafqat

(57)      ABSTRACT

The invention provides a method for monitoring a location of a tool in an ultrasound image. The method includes acquiring a plurality of 2D ultrasound images by way of an ultrasound transducer, wherein at least one of the plurality of 2D ultrasound images comprises a part of the tool and
(Continued)

generating a 3D ultrasound image from said plurality of 2D ultrasound images. A first location of the tool is then identified within the 3D ultrasound image. An additional 2D ultrasound image, and location information relating to the location of the ultrasound transducer during capture of the additional 2D ultrasound image, is then acquired and the 3D ultrasound image updated based on the additional 2D ultrasound image and the location information. A location of the tool with respect to the additional 2D ultrasound image is then identified within the updated 3D ultrasound image based only on imaging data of the updated 3D ultrasound image.

14 Claims, 4 Drawing Sheets

(52) U.S. Cl.
CPC . *A61B 2090/367* (2016.02); *A61B 2562/0219* (2013.01)

(58) Field of Classification Search
CPC .......... A61B 2562/0219; A61B 8/5223; A61B 2017/3413; A61B 2034/2048; A61B 2034/2065; A61B 2090/378; A61B 34/20; G01S 15/8993
See application file for complete search history.

(56) References Cited

U.S. PATENT DOCUMENTS

| 6,013,032 | A | 1/2000 | Savord |
| 6,283,919 | B1 | 9/2001 | Roundhill et al. |
| 6,443,896 | B1 | 9/2002 | Detmer |
| 6,458,083 | B1 | 10/2002 | Jago et al. |
| 6,530,885 | B1 | 3/2003 | Entrekin et al. |
| 6,623,432 | B2 | 9/2003 | Powers et al. |
| 6,733,458 | B1 | 5/2004 | Steins et al. |
| 2002/0049375 | A1 | 4/2002 | Strommer et al. |
| 2010/0249595 | A1 | 9/2010 | Xu et al. |
| 2012/0004539 | A1 | 1/2012 | Gardi et al. |
| 2017/0309062 | A1 | 10/2017 | Ng et al. |
| 2018/0333141 | A1* | 11/2018 | Pardasani ............ A61B 8/0841 |

OTHER PUBLICATIONS

Vrooijink, et al., "Needle path planning and steering in a three-dimensional non-static environment using two-dimensional ultrasound images", HHS Public Access, Int J. Rob Res., Sep. 2014, 33(10), pp. 1361-1374.

Pourtaherian, et al., Gabor-Based Needle Detection and Tracking in Three-Dimensional Ultrasound Data Volumes, 2014 IEEE International Conference on Image Processing, Oct. 27, 2014, pp. 3602-3606.

International Search and Written Opinion for International Application No. PCT/EP2019/074149, filed Sep. 11, 2019, 11 pages.

Lindseth, et al., "Probe calibration for freehand 3-D ultrasound", Ultrasound in Medicine & Biology, vol. 29, Issue 11, Nov. 2003, pp. 1607-1623. (Abstract).

Weng, et al., "US extended-field-of-view imaging technology", Radiology 203(3), pp. 427-441. (Abstract).

Rivaz, et al., "Novel reconstruction and feature techniques for sensorless freehand 3D ultrasound," Proc. SPIE 7629, Medical Imaging 2010: Ultrasonic Imaging, Tomography, and Therapy. (Abstrac).

Housden, et al., "Sensorless Reconstruction of Unconstrained Freehand 3D Ultrasound Data", In Ultrasound in Medicine & Biology, vol. 33, Issue 3, 2007, pp. 408-419.

Conrath, et al., "Towards Improving the Accuracy of Sensorless Freehand 3D Ultrasound by Learning", International Workshop on Machine Learning in Medical Imaging, 2012, vol. 7588, pp. 78-85. (Abstract).

Prevost, et al, "Deep Learning for Sensorless 3D Freehand Ultrasound Imaging", Medical Image Computing and Computer-Assisted Intervention—MICCAI 2017. MICCAI 2017, Lecture Notes in Computer Science, vol. 10434, 8 pages.

Prevost, R. et al., "3D freehand ultrasound without external tracking using deep learning," Medical Image Analysis, 2018, vol. 48, pp. 187-202.

Liu, G. et al., "Image Inpainting for Irregular Holes Using Partial Convolutions," Computer Vision—ECCV 2018, LNCS, 2018, vol. 11215, pp. 89-105.

Rivaz, H. et al., "Novel reconstruction and feature exploitation techniques for sensorless freehand 3D ultrasound," Proc. SPIE 7629, Medical Imaging 2010: Ultrasonic Imaging, Tomography, and Therapy, 76291D, 2010, 9 pages.

Housden, J. et al., "Sensorless Reconstruction of Unconstrained Freehand 3D Ultrasound Data," Ultrasound in Medicine & Biology, 2007, vol. 33, Issue 3, pp. 408-419.

Weng, L. et al., "US Extended-Field-of-View Imaging Technology," Radiology, 1997, vol. 203, pp. 877-880.

* cited by examiner

SYSTEMS AND METHODS FOR TRACKING A TOOL IN AN ULTRASOUND IMAGE

RELATED APPLICATIONS

This application is the U.S. National Phase application under 35 U.S.C. § 371 of International Application No. PCT/EP2019/074149, filed on Sep. 11, 2019, which claims the benefit and priority to both Provisional Application Ser. No. 62/731,122, filed Sep. 14, 2018, and European Application No. 18200503.3, filed Oct. 15, 2018, which are incorporated by reference herein in their entireties.

FIELD OF THE INVENTION

The present invention relates to the field of ultrasound imaging, and more specifically to the field of tracking a tool within an ultrasound image.

BACKGROUND OF THE INVENTION

Ultrasound imaging is one of the most popular imaging systems for tool guidance applications. Ultrasound imaging may be used to image tools such as needles, laparoscopes, stents, and radioactive seeds used for brachytherapy. For example, ultrasound imaging may be used for needle guidance in anesthesiology, tissue ablation or for biopsy guidance, since needles are used to take tissue samples, and to deliver medicine or electrical energy to the targeted tissue inside a patient's body. During these procedures, visualization of the needle and its tip is very important in order to minimize risk to the patient and improve health outcomes.

Typically, 2D ultrasound guidance is used to visualize a tool while a procedure is being conducted. However, this mode of imaging has a number of drawbacks. In particular, 2D imaging has a limited field of view; after a successful alignment and localization of the tool in the ultrasound image and while moving the tool or assessing the target, any undesired hand motion of the person conducting the procedure may cause misalignment of the tool and the ultrasound transducer such that parts of the tool are excluded from the ultrasound image. This may lead to incorrect placement of the tool. Furthermore, during the procedure, the focus of the operator may be diverted from treatment, as they may be distracted by searching for the tool in the ultrasound image.

External tool tracking systems also have a number of disadvantages, since they require additional equipment, which adds to the cost of the ultrasound imaging system. Further, a specialized needle comprising additional sensors is required. Limiting the physician to the use of a specialized needle will likely add to the cost of the procedure.

Alternative methods have been proposed utilizing a 3D ultrasound system, in which the needle can be easily captured within a large field of view and advanced image-based tracking systems would detect and visualize the needle. However, these methods require the utilization of 3D ultrasound transducers, which are typically not readily available for use in needle guidance procedures and may add to the cost of a procedure.

There is therefore a need for a tool tracking method that utilizes a typical 2D ultrasound imaging system, whilst also reducing the skill level required by the user to reliably capture images containing the tool and without requiring significant additional hardware.

Document US 2002/049375, hereby incorporated by reference, discloses a medical imaging and navigation system including a processor, a medical positioning system, a two-dimensional imaging system and an inspected organ monitor interface.

SUMMARY OF THE INVENTION

The invention is defined by the claims.

According to examples in accordance with an aspect of the invention, there is provided a method for monitoring a location of a tool in an ultrasound image, the method comprising:

acquiring a plurality of 2D ultrasound images by way of an ultrasound transducer, wherein at least one of the plurality of 2D ultrasound images comprises a part of the tool;

generating a 3D ultrasound image based on the plurality of 2D ultrasound images;

identifying a first location of the tool within the 3D ultrasound image;

acquiring an additional 2D ultrasound image and location information relating to the location of the ultrasound transducer during capture of the additional 2D ultrasound image;

updating the 3D ultrasound image based on the additional 2D ultrasound image and the location information; and identifying a location of the tool with respect to the additional 2D ultrasound image within the updated 3D ultrasound image based only on imaging data of the updated 3D ultrasound image.

The method provides for a computationally efficient way to track a tool, such as a needle, within an ultrasound image.

Typical methods rely solely on 2D ultrasound images, which require a high level of skill to acquire in order to accurately capture an image of the tool, or 3D transducer technology, which is bulky, expensive and has a limited refresh rate.

By generating a 3D image based on a plurality of 2D images, it is possible to reduce the computational load on an ultrasound imaging system, whilst also simplifying the tracking of the tool.

Further, the updating of the 3D model using subsequently acquired 2D images allows the tool to be tracked as it moves and as the location from which the subsequent 2D images are taken moves. In this way, the method provides for convenient, accurate and fast guidance of the tool using a conventional 2D US transducer with minimal (or no) change required to the typical clinical work flow that may be used with any existing interventional tool and 2D ultrasound transducer.

In addition, the determining of the location of the tool with respect to the additional 2D ultrasound image allows the position of the transducer to be tracked relative to the position of the tool. Thus, as the transducer is manipulated, the relative position of the transducer to the tool may be known, thereby allowing more simple and accurate acquisition of the tool within the additional 2D ultrasound image. Further, as the additional 2D ultrasound image may include an area of interest, for example a tumor for biopsy, the tool may be guided to the area of interest using the relative location information.

Further, as the identifying of the tool is based only on the imaging data of the updated 3D ultrasound image, there is no requirement for a dedicated tool tracking system, such as a medical positioning system, in order to perform the method. Thus, the method may be performed by any ultrasound system without requiring additional specialist hardware, thereby increasing the availability and convenience of utilizing a tool tracking method.

In an embodiment, identifying the location of the tool comprises:

identifying a tool shadow within the updated 3D ultrasound image; and identifying the location of the tool based on the tool shadow.

In this way, the location of the tool may be identified based only on the imaging data of the updated 3D ultrasound image.

In an embodiment, the additional 2D ultrasound image is received from a different transducer location to the location for the plurality of 2D ultrasound images and the method further comprises determining a change in location of the ultrasound transducer, wherein the change in location forms at least part of the location information.

In this way, both the motion of the tool and the transducer may be accounted for.

In a further embodiment, the determination of a change in location of the ultrasound transducer is performed using one or more of:

block matching;

feature tracking;

motion tracking;

speckle decorrelation;

feature exploitation;

machine learning; and deep learning.

In this way, it is possible to determine a change in location of the ultrasound transducer by way of image processing or motion tracking techniques.

In an arrangement, the location information of the additional 2D ultrasound image comprises translation information relating to the ultrasound transducer.

In this way, it is possible to monitor the position of the transducer with respect to the tool, thereby increasing the accuracy of the monitoring of the tool within the ultrasound image.

In a further, or other, arrangement, the location information of the additional 2D ultrasound image comprises orientation information relating to the ultrasound transducer.

In this way, the accuracy of the monitoring of the tool within the ultrasound image may be further increased.

In an embodiment, the method further comprises displaying the location of the tool with respect to the additional 2D ultrasound image within the updated 3D ultrasound image to a user.

In this way, the user may be informed as to the updated relative positions of the transducer and the tool.

In an arrangement, the method further comprises displaying the updated 3D ultrasound image to the user.

In this way, it is possible to monitor the location of the tool within the context of the 3D ultrasound image, thereby increasing the information available to the user when manipulating the tool.

According to examples in accordance with an aspect of the invention, there is provided a computer program comprising computer program code means which is adapted, when said computer program is run on a computer, to implement the method described above.

According to examples in accordance with an aspect of the invention, there is provided an ultrasound imaging system adapted to monitor a location of a tool in an ultrasound image, the system comprising:

an ultrasound probe comprising an ultrasound transducer adapted to obtain a plurality of 2D ultrasound images, wherein at least one of the plurality of 2D ultrasound images comprises a part of the tool;

a processor, wherein the processor is adapted to:

generate a 3D ultrasound image based on the plurality of 2D ultrasound images;

identify a first location of the tool within the 3D ultrasound image;

update the 3D ultrasound image based on an additional 2D ultrasound image acquired by way of the ultrasound probe and location information relating to the location of the ultrasound transducer during capture of the additional 2D ultrasound image; and identify a location of the tool with respect to the additional 2D ultrasound image within the updated 3D ultrasound image within the updated 3D ultrasound image based only on imaging data of the updated 3D ultrasound image.

In an embodiment, the processor is further adapted to:

receive the additional 2D ultrasound image from a different transducer location to the location for the plurality of 2D ultrasound images; and determine a change of location of the ultrasound probe, wherein the change in location forms at least part of the location information.

In an arrangement, the system further comprises a sensor adapted to acquire the location information.

In a further arrangement, the sensor is an accelerometer or a position sensor.

In an embodiment, the system further comprises a display adapted to display the location of the tool with respect to the additional 2D ultrasound image within the updated 3D ultrasound image to a user.

In a further embodiment, the display is further adapted to display the updated 3D ultrasound image to the user.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
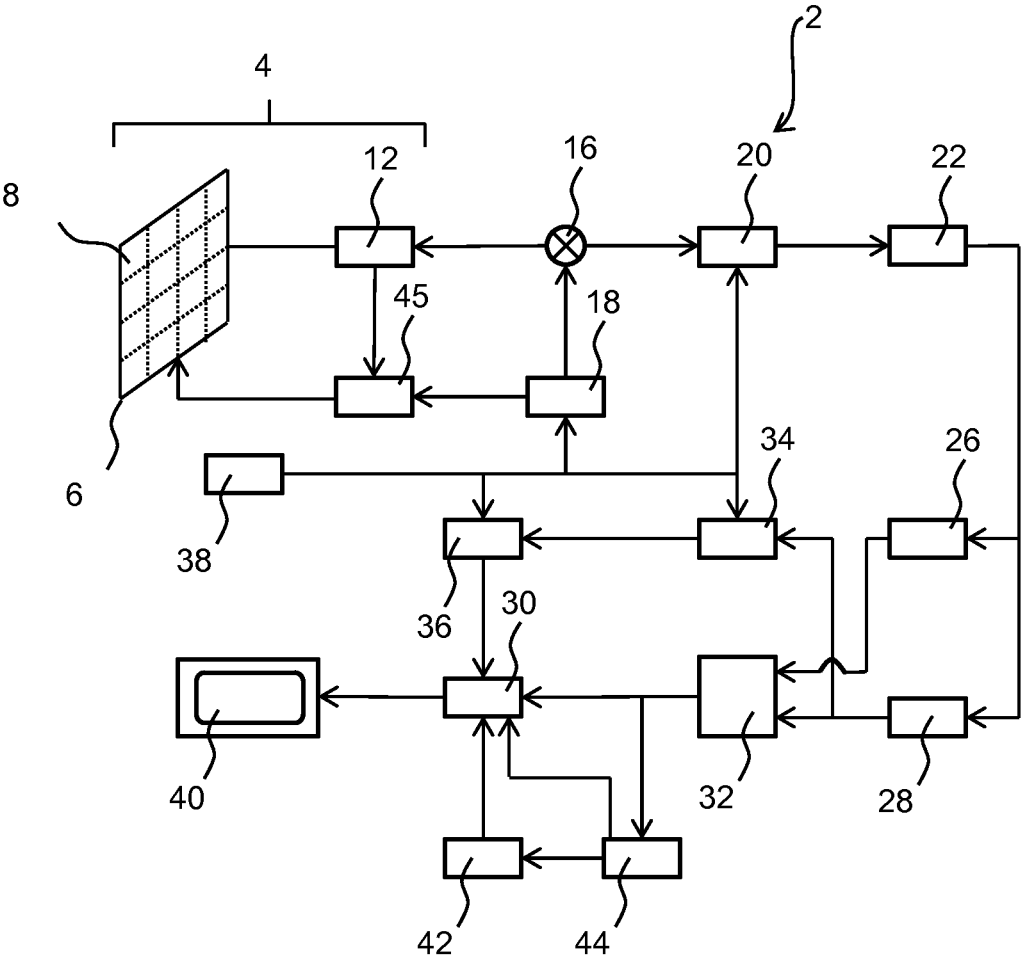
FIG. 1 shows an ultrasound diagnostic system to explain the general operation.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a method for monitoring a location of a tool in an ultrasound image. The method includes acquiring a plurality of 2D ultrasound images by way of an ultrasound transducer, wherein at least one of the plurality of 2D ultrasound images comprises a part of the tool, and generating a 3D ultrasound image from said plurality of 2D ultrasound images. A first location of the tool is then identified within the 3D ultrasound image. An additional 2D ultrasound image, and location information relating to the location of the ultrasound transducer during capture of the additional 2D ultrasound image, is then acquired and the 3D ultrasound image updated based on the additional 2D ultrasound image and the location information. A location of the tool with respect to the additional 2D ultrasound image is then identified within the updated 3D ultrasound image based only on imaging data of the updated 3D ultrasound image.

As the above method may be employed in an ultrasound imaging system, the general operation of an exemplary ultrasound system will first be described, with reference to FIG. 1, and with emphasis on the signal processing function of the system since this invention relates to the processing of the signals measured by the transducer array.

The system comprises an array transducer probe 4 which has a transducer array 6 for transmitting ultrasound waves and receiving echo information. The transducer array 6 may comprise CMUT transducers; piezoelectric transducers, formed of materials such as PZT or PVDF; or any other suitable transducer technology. In this example, the transducer array 6 is a two-dimensional array of transducer elements 8 capable of scanning either a 2D plane or a three dimensional volume of a region of interest. In another example, the transducer array may be a 1D array.

The transducer array 6 is coupled to a microbeamformer 12 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. Further, the system includes a transmit/receive (T/R) switch 16, which the microbeamformer 12 can be coupled to and which switches the array between transmission and reception modes, and protects the main beamformer 20 from high energy transmit signals in the case where a microbeamformer is not used and the transducer array is operated directly by the main system beamformer. The transmission of ultrasound beams from the transducer array 6 is directed by a transducer controller 18 coupled to the microbeamformer by the T/R switch 16 and a main transmission beamformer (not shown), which can receive input from the user's operation of the user interface or control panel 38. The controller 18 can include transmission circuitry arranged to drive the transducer elements of the array 6 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below. Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 18 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 18 can be coupled to control a DC bias control 45 for the transducer array. The DC bias control 45 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 12 and are then passed to a main receive beamformer 20 where the partially beamformed signals from individual patches of transducers are combined into a fully beamformed signal, referred to as radio frequency (RF) data. The beamforming performed at each stage may be carried out as described above, or may include additional functions. For example, the main beamformer 20 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 22. The signal processor 22 can process the received echo signals in various ways, such as: band-pass filtering; decimation; I and Q component separation; and harmonic signal separation, which acts to separate linear and nonlinear signals so as to enable the identification of non-linear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 6 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 26 and a Doppler processor 28. The B mode processor 26 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 40. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow in addition to structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 6 and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

Figure 2:
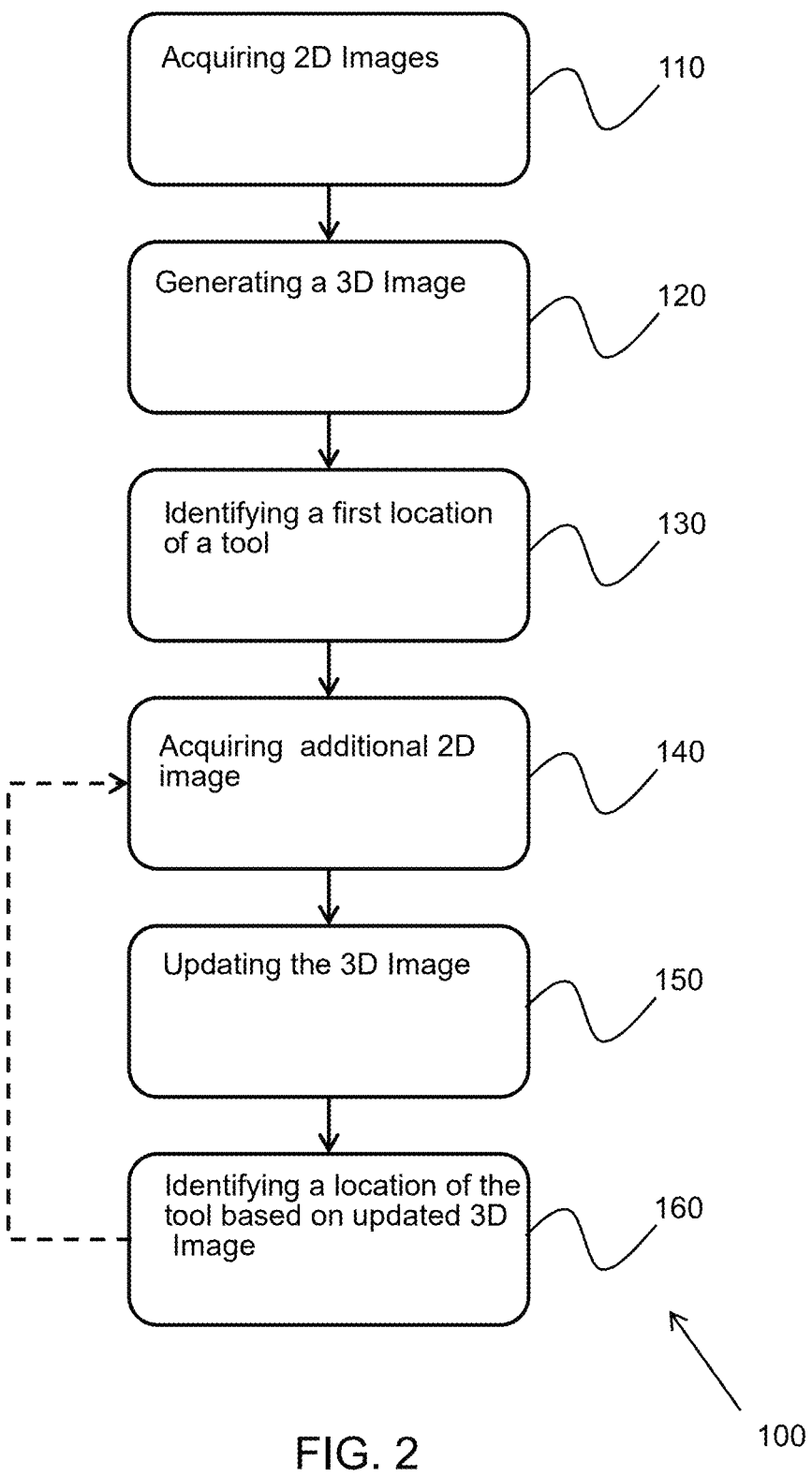
FIG. 2 shows a method of the invention.

FIG. 2 shows a method 100 for monitoring a location of a tool in an ultrasound image.

The method begins in step 110 with the acquisition of a plurality of 2D ultrasound images. The plurality of 2D ultrasound images may be captured by an ultrasound probe 4 such as the probe described above with reference to FIG. 1.

The plurality of 2D ultrasound images are captured in the vicinity of the tool, meaning that at least one of the plurality of 2D ultrasound images comprises a least part of the tool. By way of example, the tool may be a needle being used to collect a tissue sample from a given target area. By acquiring the plurality of 2D ultrasound images from the vicinity of the target area, the needle will be captured in at least one of the images.

The method then proceeds to step 120, where a 3D ultrasound image is generated based on the plurality of 2D ultrasound images. The 2D ultrasound images may be captured during an initial freehand acquisition. The 2D ultrasound images may then form image slices, wherein image data may be interpolated between the images in order to generate the full 3D ultrasound image.

The 3D ultrasound image may be generated from the plurality of 2D ultrasound images using any suitable method. For example, the 3D ultrasound image may be generated using an interpolation method as described in R. Prevost et al "3D freehand ultrasound without external tracking using deep learning", Medical Image Analysis 48 (2018), 187-202. Alternatively, the 3D ultrasound image may be generated using an image inpainting method as described in Liu, G. et al. at Liu, G., Reda, F. A., Shih, K. J., Wang, T., Tao, A., & Catanzaro, B. (2018 October 6). Image Inpainting for Irregular Holes Using Partial Convolutions. Computer Vision—ECCV 2018.

In step 130 a first location of the tool is identified within the 3D ultrasound image.

An image-based tool detection technique localizes the tool, such as a needle, in the 3D model. Tool localization in the constructed 3D volume may be performed successfully as soon as sufficient length of the tool is captured within the model. The relative position of the needle with respect to the 2D US transducer may be provided to the user for optimizing a manipulation of the transducer to correctly visualize the complete tool.

A potential method for identifying the tool within the 3D ultrasound image is discussed below with reference to FIG. 3, described further below.

In step 140, an additional 2D ultrasound image is acquired. In addition, location information relating to the location of the ultrasound probe during the acquisition of the additional 2D ultrasound image is recorded.

For example, following the acquisition of the plurality of 2D ultrasound images, the user may move the ultrasound probe in order to capture the additional 2D ultrasound image. In other words, the additional 2D ultrasound image may be received from a different transducer location to the locations of the plurality of 2D ultrasound images.

Put another way, a change in location of the ultrasound transducer preceding the acquisition of the additional 2D ultrasound image may be determined and form at least part of the location information. In this way, the location of the additional 2D ultrasound image relative to the 3D ultrasound image may be known.

The change in location of the ultrasound transducer may be determined using one or more of: block matching; feature tracking; motion tracking; speckle decorrelation; feature exploitation; machine learning; and deep learning.

The motion tracking may be performed by devoted motion sensors, such as add-on accelerometers, accelerometers integrated into the ultrasound probe, or position sensors (for example, optical motion sensors).

The motion tracking may also be performed solely using image processing. For example, movements of the transducer in a lateral direction (across the surface of a subject) may be tracked using a block matching algorithm, which is a way of locating matching macroblocks in a sequence of images, such as the 2D ultrasound images, for motion estimation. The algorithm involves dividing an image, for example the additional 2D ultrasound image, into macroblocks and comparing each macroblock to a corresponding macroblock of another image, for example one of the plurality of 2D ultrasound images. A vector is then created modelling the movement of a macroblock from one location to another. The vector may then be used to estimate a change in location of the ultrasound probe between the acquisition of the plurality of 2D ultrasound images and the additional 2D ultrasound image.

In addition, movements of the transducer in the elevation direction (toward and away from the surface of the subject) may also be tracked. It is known that ultrasound beams have a specified thickness defined by the elevation resolution of the transducer and echoes are registered in the image plane at each beam position where the beam overlaps the tissue structures. This concept is illustrated further with reference to FIGS. 4A and 4B, described further below.

Thus, when the transducer moves in the elevation direction, all of the structures within the thickness of the beam width are registered on the image plane with different intensities, wherein the structures show a maximum intensity when located at the middle of the beam width and a minimum intensity when the beam overlap is minimum. This enables tracking of structures that gradually appear and disappear from an image plane using image processing techniques, such as speckle decorrelation (as described in Li, M. "System and method for 3-D medical imaging using 2-D scan data", U.S. Pat. No. 5,582,173, application number 529778 (1995) and Hassan Rivaz et al, "Novel reconstruction and feature exploitation techniques for sensorless freehand 3D ultrasound," Proc. SPIE 7629, Medical Imaging 2010: Ultrasonic Imaging, Tomography, and Therapy, 76291D (12 Mar. 2010)) and feature exploitation (as described in R. James Housden et al, Sensorless Reconstruction of Unconstrained Freehand 3D Ultrasound Data, In Ultrasound in Medicine & Biology, Volume 33, Issue 3, 2007, Pages 408-419, ISSN 0301-5629). Further, it is possible to employ machine learning and/or deep learning approaches for image analysis in order to estimate the motion of the probe.

Further, the thickness of the ultrasound beam width can be increased for improving the accuracy and robustness of the various tracking algorithms.

The location information of the additional 2D ultrasound image may include both translation and orientation information relating to the ultrasound transducer. The translation may be in a lateral direction or an elevation direction and the orientation may include a tilt or rotation of the ultrasound probe. In other words, it is possible to track both the position and orientation of the ultrasound probe during the acquisition of the 2D ultrasound images.

In step 150, the 3D ultrasound image is updated based on the additional 2D ultrasound image acquired in step 140.

The additional 2D ultrasound image may be registered into the 3D ultrasound image using its relative position and orientation with respect to a previously acquired 2D ultrasound image of the plurality of 2D ultrasound images. The 3D ultrasound image may then be updated to model the acquired region of interest constructed from the previous 2D ultrasound image acquisitions. The 3D ultrasound image may be updated in a similar manner to how the original 3D ultrasound image was generated using the plurality of 2D ultrasound images.

In other words, when the additional 2D ultrasound image is acquired, its position is determined with respect to the generated 3D ultrasound image. The 3D ultrasound image is then updated using the additional 2D ultrasound image and its location information.

The method proceeds to step 160, where a location of the tool with respect to the additional 2D ultrasound image is identified within the updated 3D ultrasound image based only on imaging data of the updated 3D ultrasound image.

The imaging data may comprise any data associated with the generation of the 3D ultrasound image. For example, imaging data may include: pixel values of the plurality of 2D ultrasound images; pixel values of the additional 2D ultrasound image; voxel values of the 3D ultrasound image; voxel values of the updated 3D ultrasound image; imaging parameters of the ultrasound probe; metadata associated with the ultrasound images; a position and/or orientation of the ultrasound probe during image capture; a user input associated with an ultrasound image; a segmented structure within an ultrasound image; and the like.

For example, the location of the tool may be identified based only on the pixel values of the plurality of 2D ultrasound images and the additional 2D ultrasound image. Alternatively, or in addition, the location of the tool may be identified based on the voxel values of the updated 3D ultrasound image.

In other words, the position of the tool is determined (within the 3D ultrasound image) with respect to the newly acquired 2D ultrasound image.

The motion of the tool is largely restricted to a given plane when located in the tissue of a subject. Thus, the position of the plane in which the tool is located within the 3D ultrasound image does not change significantly with respect to newly acquired 2D image when the tool moves.

However, as the transducer used to acquire the ultrasound images has an unrestricted range of movement, the position of the transducer relative to the tool may change significantly.

Thus, the identifying of the relative position of the transducer (when acquiring the additional 2D ultrasound image) and the tool may serve to guide the user in the manipulation of both the transducer, for imaging the desired region, and the tool, for reaching the desired region.

By way of example, a tissue sample may need to be retrieved from a tumor within a subject. A tool, such as a needle in this case, is inserted by a user proximate to the known location of the tumor and an ultrasound transducer used to image the region surrounding the tool and the tumor.

The ultrasound transducer acquires a plurality of 2D ultrasound images and a 3D ultrasound image is generated based on the plurality of 2D ultrasound images. The location of the needle is identified within the 3D ultrasound image and may be shown to the user.

The user may then move the ultrasound transducer in order to capture an additional 2D ultrasound image. For example, the full tumor may not be contained within the original 3D ultrasound image. Thus, the user may move the transducer in order to acquire an image of the desired area. The location of the newly acquired 2D ultrasound image may be determined and used to update the 3D ultrasound image for display to the user.

Further, the location of the newly acquired 2D ultrasound image relative to the tool is also identified. This may then provide an indication of the displacement between the area within the newly acquired 2D ultrasound image and the tool. Thus, the user may be provided with a guidance of how to move the tool to the area imaged in the additional 2D ultrasound image.

The tool identification may be performed as in step 130. The image-based tool detection technique localizes the tool, such as a needle, in the 3D model with respect to the current position of the 2D US transducer. Once again, a potential tool detection technique is described below with reference to FIG. 3.

Following step 160, the method may return to step 140 where a new additional 2D ultrasound is acquired. In other words, the 3D model may be repeatedly updated and the position of the tool tracked based on a sequence of incoming 2D ultrasound images.

In addition, the second location of the tool and the 3D ultrasound image may be displayed to a user, thereby allowing the user to accurately manipulate the tool and ultrasound probe to reach a desired location.

Alternatively, the position and orientation of the transducer may be determined to construct a one-time full 3D ultrasound volume of the region of interest including the tool. The image-based tool detection system is then utilized to visualize the needle in 3D with respect to other important structures in the volume. This may be utilized when the user is seeking a confirmation regarding the accurate placement of the needle tip for procedures such as injections or performing biopsies.

Figure 3:
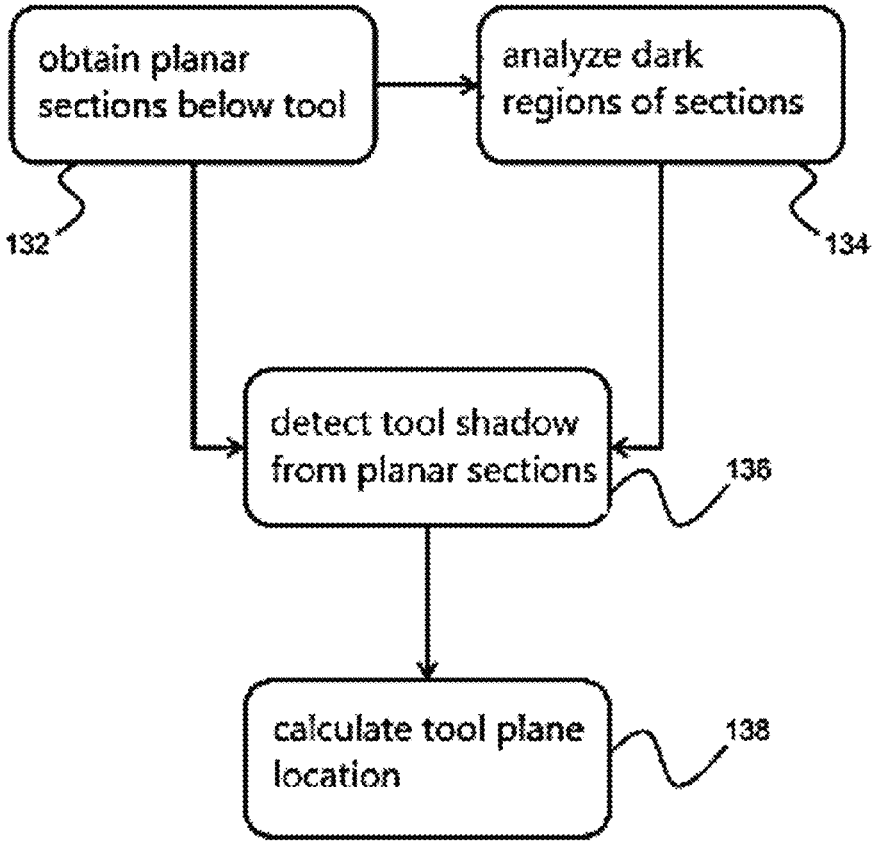
FIG. 3 shows a further method of the invention.
Figure 3:

FIG. 3 shows step 130 of FIG. 2 in more detail, wherein the first location of the tool is determined within the 3D ultrasound image.

In step 132, a set of planar sections is obtained from the 3D ultrasound image, generated using the plurality of 2D ultrasound images. The planar sections represent sections of the generated 3D volume located below the tool, which are perpendicular to the transmission direction of the ultrasound waves emitted by the ultrasound imaging system. The shadow of the tool is most visible in these planar sections of the 3D image. Therefore, using these planar sections to locate the tool enables fast and accurate identification of the tool shadow. The planar sections are obtained at different depths of the 3D image, providing a set of planar sections. The planar sections may simply be the acquired plurality of 2D ultrasound images.

In step 134, the planar sections obtained in step 132 are analyzed to detect dark regions of the planar sections that may represent a shadow of the tool. In sections beneath the tool, a shadow of the tool will appear as an ellipsoidal blob, which is relatively dark compared to a neighboring region of the 3D image. After de-noising the image and performing analysis techniques such as negative thresholding, line detection or segmentation techniques, dark regions having the properties typical of the tool shadow can be identified. Further enhancement may be implemented by examining the size, width and shape of the dark regions, since the size, width and shape of the tool is known, meaning an expected size, width and shape of the shadow can be calculated. However, not all the dark regions present in the planar sections correspond to a shadow of the tool. Therefore, some of the detected dark regions do not form part of the tool shadow.

In step 136, the dark regions detected in step 134 are processed to identify which of the dark regions correspond to the tool shadow. By identifying at least one tool shadow region, it is possible to determine the location of a plane of the 3D ultrasound image which represents the full length of the needle along an axis of the volume.

The location of the tool section plane may be determined based on the position of a single detected tool shadow region, or multiple tool shadow regions from different planar sections which together form a detected overall shadow.

There are different ways to process the planar sections to identify the dark regions corresponding to tool shadows. These tool shadow regions are a subset of the detected dark regions. To identify this subset, a random sample and consensus algorithm (RANSAC) is performed on the data set. In the RANSAC method, a fitting model is determined and elements of the dataset are checked to determine which elements are consistent with the fitting model. The tool shadow region subset is a subset of the dataset that has minimal outliers.

In one example, in order to locate the tool shadow region subset, a possible tool plane is chosen, and the number of detected dark regions in sections perpendicular to the tool plane section that are consistent with the possible tool plane section are counted. Alternatively, or additionally, the number of sections perpendicular to the transmission direction of ultrasound waves emitted by the ultrasound imaging system that include dark regions consistent with the possible tool plane are counted.

This process may be repeated for several iterations until the possible tool plane with the maximum number of inliers is identified; this is the actual tool plane. The dark regions that intersect with the tool plane section are tool shadow regions which form an overall tool shadow. Therefore, by identifying the plane that includes the overall tool shadow, the orientation of the tool plane section is determined based on the tool shadow regions.

In step 138, a section of the volume parallel to the ultrasound beams and containing the full length of the detected overall shadow is calculated. This section is the tool plane, which contains the full-length needle and the tip. Other views of the needle may also be located based on the position of the tool plane section. In this way, the first location of the tool may be identified within the 3D ultrasound image. Further, this method may be repeated for identifying the second location of the tool within the 3D ultrasound image.

Figure 4A:
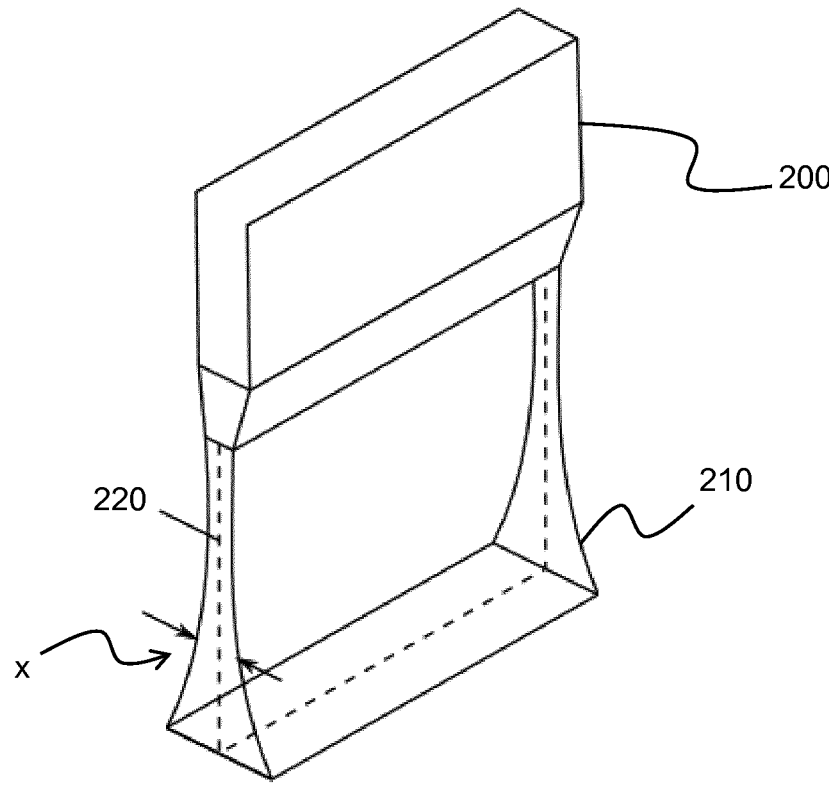
FIGS. 4A and 4B show a schematic representation of an ultrasound transducer and echo intensity.

FIG. 4A shows an ultrasound transducer 200 for generating an ultrasonic beam 210 having a beam width, x. The imaging plane 220 is shown at the center of the ultrasonic beam.

Figure 4B:
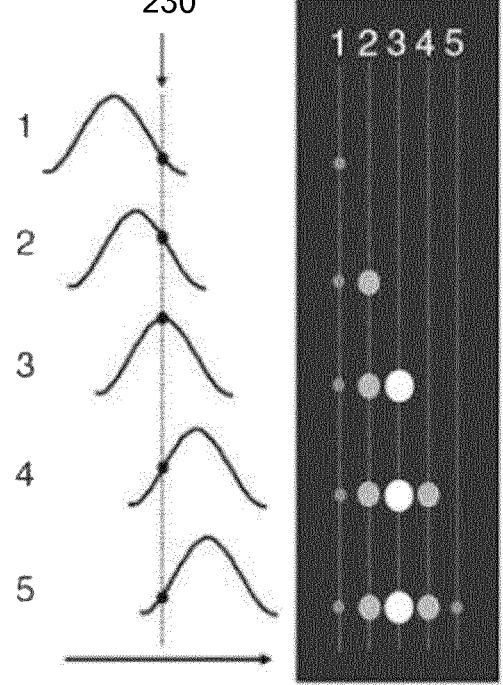

FIG. 4B shows a series of images, where the imaging target 230 is located at various positions within an ultrasonic beam 210, wherein the peak of the wave represents the center of the ultrasonic beam. Further, there is shown a representation of the intensity of the echo generated by the target when located at a given positon within the ultrasonic beam. When the target is located at positions 1 and 5, the intensity is at a minimum; whereas, when the target is located at position 3 (the peak of the wave and so the center of the ultrasonic beam) the echo intensity is at a maximum.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for monitoring a location of a tool in an ultrasound image, the method comprising:

acquiring a plurality of 2D ultrasound images by way of an ultrasound transducer, wherein at least one of the plurality of 2D ultrasound images comprises a part of the tool;

generating a 3D ultrasound image based on the plurality of 2D ultrasound images;

identifying a first location of the tool within the 3D ultrasound image;

acquiring an additional 2D ultrasound image and location information relating to the location of the ultrasound transducer during capture of the additional 2D ultrasound image;

updating the 3D ultrasound image based on the additional 2D ultrasound image and the location information; and identifying a location of the tool with respect to the additional 2D ultrasound image within the updated 3D ultrasound image based only on imaging data of the updated 3D ultrasound image, and wherein identifying the location of the tool comprises identifying a tool shadow within the updated 3D ultrasound image, and identifying the location of the tool based on the tool shadow, wherein the imaging data is selected from one or more of: pixel values of the plurality of 2D ultrasound images; pixel values of the additional 2D ultrasound image; voxel values of the 3D ultrasound image; voxel values of the updated 3D ultrasound image; imaging parameters of the ultrasound probe; metadata associated with the ultrasound images; a position of the ultrasound probe during image capture; an orientation of the ultrasound probe during image capture; a user input associated with an ultrasound image; and a segmented structure within an ultrasound image, and further wherein the additional 2D ultrasound image is received from a different transducer location to the location for the plurality of 2D ultrasound images and the method further comprises determining a change in location of the ultrasound transducer, wherein the change in location forms at least part of the location information, and wherein the determination of a change in location of the ultrasound transducer is performed using one or more of block matching, feature tracking, motion tracking, speckle decorrelation, feature exploitation, machine learning, and deep learning.

2. A method as claimed in claim 1, wherein the location information of the additional 2D ultrasound image comprises translation information relating to the ultrasound transducer.

3. A method as claimed in claim 1, wherein the location information of the additional 2D ultrasound image comprises orientation information relating to the ultrasound transducer.

4. A method as claimed in claim 1, wherein the method further comprises displaying the location of the tool with respect to the additional 2D ultrasound image within the updated 3D ultrasound image to a user.

5. A method as claimed in claim 1, wherein the method further comprises displaying the updated 3D ultrasound image to the user.

6. The method of claim 1, wherein the tool is a biopsy needle.

7. The method of claim 1, wherein the step of identifying the location of the tool based on the tool shadow further comprises identifying a relatively dark region in the plurality of 2D ultrasound images compared to a neighboring region of the 3D ultrasound image, and identifying the dark region as corresponding to the shadow of the tool.

8. The method of claim 7, wherein the step of identifying the dark region as corresponding to the shadow of the tool is performed by a random sample and consensus (RANSAC) method.

9. The method of claim 7, further comprising identifying an actual tool plane as one of the plurality of 2D ultrasound images having a maximum number of inliers, identifying a tool shadow region that intersects with the actual tool plane section, and determining an orientation of the tool plane section based on the tool shadow region.

10. A non-transitory computer readable medium comprising a computer program code means which is adapted, when said computer program code means is run on a computer, to implement a method for monitoring a location of a tool in an ultrasound image, the method comprising the steps of:

acquiring a plurality of 2D ultrasound images by way of an ultrasound transducer, wherein at least one of the plurality of 2D ultrasound images comprises a part of the tool;

generating a 3D ultrasound image based on the plurality of 2D ultrasound images;

identifying a first location of the tool within the 3D ultrasound image;

acquiring an additional 2D ultrasound image and location information relating to the location of the ultrasound transducer during capture of the additional 2D ultrasound image;

updating the 3D ultrasound image based on the additional 2D ultrasound image and the location information; and identifying a location of the tool with respect to the additional 2D ultrasound image within the updated 3D ultrasound image based only on imaging data of the updated 3D ultrasound image, and wherein identifying the location of the tool comprises identifying a tool shadow within the updated 3D ultrasound image, and identifying the location of the tool based on the tool shadow, wherein the imaging data is selected from one or more of: pixel values of the plurality of 2D ultrasound images; pixel values of the additional 2D ultrasound image; voxel values of the 3D ultrasound image; voxel values of the updated 3D ultrasound image; imaging parameters of the ultrasound probe; metadata associated with the ultrasound images; a position of the ultrasound probe during image capture; an orientation of the ultrasound probe during image capture; a user input associated with an ultrasound image; and a segmented structure within an ultrasound image, and further wherein the additional 2D ultrasound image is received from a different transducer location to the location for the plurality of 2D ultrasound images and the method further comprises determining a change in location of the ultrasound transducer, wherein the change in location forms at least part of the location information, and wherein the determination of a change in location of the ultrasound transducer is performed using one or more of block matching, feature tracking, motion tracking, speckle decorrelation, feature exploitation, machine learning, and deep learning.

11. An ultrasound imaging system adapted to monitor a location of a tool in an ultrasound image, the system comprising:

an ultrasound probe comprising an ultrasound transducer adapted to obtain a plurality of 2D ultrasound images, wherein at least one of the plurality of 2D ultrasound images comprises a part of the tool;

a processor, wherein the processor is adapted to:

generate a 3D ultrasound image based on the plurality of 2D ultrasound images;

identify a first location of the tool within the 3D ultrasound image;

update the 3D ultrasound image based on an additional 2D ultrasound image acquired by way of the ultrasound probe and location information relating to the location of the ultrasound transducer during capture of the additional 2D ultrasound image; and identify a location of the tool with respect to the additional 2D ultrasound image within the updated 3D ultrasound image based only on imaging data of the updated 3D ultrasound image, and wherein identifying the location of the tool comprises identifying a tool shadow within the updated 3D ultrasound image, and identifying the location of the tool based on the tool shadow, wherein the imaging data is selected from one or more of:

pixel values of the plurality of 2D ultrasound images;

pixel values of the additional 2D ultrasound image;

voxel values of the 3D ultrasound image; voxel values of the updated 3D ultrasound image; imaging parameters of the ultrasound probe; metadata associated with the ultrasound images; a position of the ultrasound probe during image capture; an orientation of the ultrasound probe during image capture; a user input associated with an ultrasound image; and a segmented structure within an ultrasound image, and further wherein the additional 2D ultrasound image is received from a different transducer location to the location for the plurality of 2D ultrasound images and the method further comprises determining a change in location of the ultrasound transducer, wherein the change in location forms at least part of the location information, and wherein the determination of a change in location of the ultrasound transducer is performed using one or more of block matching, feature tracking, motion tracking, speckle decorrelation, feature exploitation, machine learning, and deep learning.

12. The system of claim 11, wherein the tool is a biopsy needle.

13. A system as claimed in claim 11, wherein the system further comprises a display adapted to display the location of the tool with respect to the additional 2D ultrasound image within the updated 3D ultrasound image to a user.

14. A system as claimed in claim 13, wherein the display is further adapted to display the updated 3D ultrasound image to the user.

* * * * *